United States Patent
Fuhr et al.

(10) Patent No.: US 7,634,917 B2
(45) Date of Patent: Dec. 22, 2009

(54) CRYO-DEVICE AND ASSOCIATED OPERATIONAL METHOD

(75) Inventors: Günter Fuhr, Berlin (DE); Heiko Zimmermann, St. Ingbert (DE); Young-Joo Oh, Saarbrücken (DE); Uwe Schön, Neunkirchen (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 319 days.

(21) Appl. No.: 11/576,406

(22) PCT Filed: Sep. 30, 2005

(86) PCT No.: PCT/EP2005/054947

§ 371 (c)(1),
(2), (4) Date: Apr. 13, 2007

(87) PCT Pub. No.: WO2006/037760

PCT Pub. Date: Apr. 13, 2006

(65) Prior Publication Data

US 2007/0267419 A1    Nov. 22, 2007

(30) Foreign Application Priority Data

Oct. 1, 2004    (DE) .................... 10 2004 047 965

(51) Int. Cl.
*F25D 25/00*    (2006.01)
(52) U.S. Cl. ............... 62/62; 62/371; 62/378; 62/457.2; 220/592.2
(58) Field of Classification Search .......... 62/371, 62/378, 457.2; 220/592.2
See application file for complete search history.

(56) References Cited

U.S. PATENT DOCUMENTS

| | | | | |
|---|---|---|---|---|
| 4,388,814 | A | * | 6/1983 | Schilling ............ 62/62 |
| 4,480,682 | A | * | 11/1984 | Kaneta et al. ........ 165/206 |
| 4,537,034 | A | * | 8/1985 | Crouch .............. 62/62 |
| 4,783,973 | A | * | 11/1988 | Angelier et al. ...... 62/457.9 |
| 4,799,358 | A |   | 1/1989 | Knopf et al. |
| 5,105,627 | A | * | 4/1992 | Kurita .............. 62/62 |
| 5,715,686 | A |   | 2/1998 | Arav |
| 5,979,175 | A | * | 11/1999 | Ellison ............. 62/457.7 |
| 6,065,294 | A | * | 5/2000 | Hammerstedt et al. .. 62/3.3 |
| 7,278,278 | B2 | * | 10/2007 | Wowk et al. ......... 62/371 |

(Continued)

FOREIGN PATENT DOCUMENTS

DE    3125345 A1    1/1983

(Continued)

OTHER PUBLICATIONS

Search Report of PCT/EP2005/054947.

*Primary Examiner*—Cheryl J Tyler
*Assistant Examiner*—Jonathan Koagel
(74) *Attorney, Agent, or Firm*—Caesar, Rivise, Bernstein, Cohen & Pokotilow, Ltd.

(57) ABSTRACT

The invention relates to a cryoapparatus for freezing and/or thawing a sample (1), especially in the cryopreservation of a biological sample (1), with a coolable cooling space (3) and with a sample container (10) arranged in the cooling space (3) for temporarily receiving the sample (1) when freezing or thawing the sample (1). It is suggested that the sample container (10) can be tempered separately from the cooling space. Furthermore, the invention includes an associated operating method.

28 Claims, 11 Drawing Sheets

U.S. PATENT DOCUMENTS

| | | |
|---|---|---|
| 2004/0065093 A1 | 4/2004 | Fuhr et al. |
| 2006/0156753 A1 | 7/2006 | Fuhr et al. |

FOREIGN PATENT DOCUMENTS

| | | |
|---|---|---|
| DE | 3404937 C2 | 8/1985 |
| DE | 10144925 A1 | 3/2003 |
| DE | 10332799 A1 | 2/2005 |
| EP | 0090599 A1 | 10/1983 |
| EP | 0072225 B1 | 12/1985 |
| EP | 0275829 A2 | 7/1988 |
| EP | 0181235 B1 | 4/1991 |
| EP | 0136014 B1 | 11/1993 |

\* cited by examiner

CRYO-DEVICE AND ASSOCIATED OPERATIONAL METHOD

BACKGROUND OF THE INVENTION

The invention relates to a cryoapparatus for freezing and thawing a sample, especially in the cryopreservation of a biological sample, as well as to an associated operating method.

In the known cryopreservation biological samples are frozen while maintaining vitality and subsequently thawed out again as needed while maintaining vitality. Examples of usage for such a cryopreservation are the storage of embryos for stem cell research or the preservation of sperm for a subsequent artificial fertilization. It is important for the maintenance of vitality in cryopreservation that predetermined chronological temperature characteristics are maintained during the freezing as well as during the thawing of the biological sample.

Therefore, so-called automatic freezers are used for the cryopreservation of biological samples that usually use liquid nitrogen with a boiling point of −196° C. as cooling agent and have a cooling space in which the temperature can be adjusted by controlling the supply of the cooling agent in order to achieve the desired chronological temperature characteristics when freezing or thawing biological samples.

During the freezing of biological samples they are inserted into the cooling space of the automatic freezer and subsequently cooled down in accordance with the given chronological temperature characteristics from a starting temperature of a freezing process to a target temperature of the freezing process. After the target temperature of the freezing process has been attained the frozen biological samples are then extracted from the cooling space of the automatic freezer and, e.g., stored in a cryotank.

During the thawing of frozen biological samples they are extracted, e.g., from a cryotank and inserted into the cooling space of the automatic freezer. The temperature of the frozen biological samples is subsequently raised in accordance with predetermined chronological temperature characteristics from a certain starting temperature of a thawing process to a target temperature of the thawing process. After the target temperature of the thawing process has been attained, the thawed sample is extracted from the cooling space of the automatic freezer and further used.

A disadvantage of the previously described known automatic freezer is that the sample is exposed during the insertion into the cooling space and during the extraction from the cooling temperature to undesirable temperature influences that thermally damage the biological sample and can adversely influence the maintenance of vitality.

Furthermore, the previously described known automatic freezer has the disadvantage of an unsatisfactory precision during the adjusting of the given chronological temperature characteristics during freezing and thawing, which is caused by the relatively large volume of the cooling space and the therewith associated problems of regulation technology.

The invention therefore has the task of providing an improved cryoapparatus for freezing and/or thawing a sample and of creating a corresponding operating method.

SUMMARY OF THE INVENTION

The invention comprises the general technical teaching of arranging a sample container in the relatively large cooling space of a cryoapparatus (e.g., of an automatic freezer) in which container the sample is frozen and/or thawed, wherein the sample container can be tempered separately from the cooling space. This means that different temperatures can be adjusted in the sample container and in the cooling space.

On the one hand, the separate adjustability of the temperature in the sample container offers the advantage that the chronological temperature characteristics during freezing and thawing that is important for the maintenance of the vitality of the biological sample must be adjusted only for the smaller volume inside the sample container, which is possible in a substantially more precise manner as concerns the regulation technology than the exact tempering of the entire cooling space of the automatic freezer.

On the other hand, the separate adjustability of the temperature in the sample container independently of the rest of the cooling space offers the advantage that during the insertion and the extraction of the sample the previously described problematic temperature effects that were damaging to vitality and result from deviations from the given start- and target temperatures can be avoided.

The cryoapparatus in accordance with the invention preferably has a lifting apparatus with which the sample container can be lowered and/or raised in the cooling space in a controlled or regulated manner.

On the one hand this vertical motion of the sample container in the cooling space makes it possible to take into account the vertical temperature stratification in the cooling space. Thus, the temperature in the cooling space decreases from the top downward so that the sample container has preferably been lowered at the end of a freezing process in order that the frozen sample can be extracted without problematic temperature effects of the surrounding medium in the cooling space. In contrast thereto, at the end of the thawing process the sample container is preferably in a raised position in order that the thawed sample can be extracted avoiding problematic temperature effects of the extremely cold medium present at the bottom of the cooling space.

On the other hand the vertical movement of the sample container by the lifting apparatus in a variant of the invention makes possible a tempering of the sample container in that the sample container is raised or lowered in accordance with the desired temperature within the vertical temperature stratification in the cooling space. Therefore, in this variant of the invention the sample container can be tempered separately from the cooling space even without a separate cooling apparatus in that the sample container is appropriately raised or lowered.

It is advantageous here if the sample container has a temperature sensor that measures the temperature in the sample container or at the level of the sample container or under it or above it in order that the vertical motion of the sample container in the cooling space can be regulated in a temperature-dependent manner.

It is especially advantageous here if several temperature sensors are attached to the sample container at different vertical distances to the sample container, which makes it possible to determine a local vertical temperature gradient. The regulation of the upward or downward motion of the sample container can then be regulated in a very sensitive manner for local temperature variations in the cooling space.

However, there is also the alternative possibility that the sample container is arranged stationarily in the cooling space, the sample container being preferably located on the bottom of the cooling space. The temperature change at the opening of the sample container is not achieved in this case by raising or lowering the sample container but rather can be realized, e.g., by a heating that heats the cooling space, the heating apparatus preferably heating only an upper partial area of the cooling space. The heating apparatus is preferably turned on when a sample is to be inserted into the sample container at the beginning of a freezing process or when the sample is extracted from the sample container at the end of a thawing process. The heating of the upper area of the cooling space then prevents a problematic thermal adverse influencing of the sample when the sample is being inserted or extracted. On the other hand, the heating apparatus is preferably turned off when the sample is extracted from the sample container at the end of a freezing process or when the sample is inserted into the sample container at the beginning of a thawing process. The turning off of the heating then also prevents the frozen sample from being thermally damaged when being inserted or extracted.

A vertical temperature stratification with a lower cold layer and an upper warm layer is preferably present in the cooling space. This is advantageous because the sample container can be raised or lowered for the extraction or the insertion of the sample into the temperature layer that comes the closest to the actual sample temperature, thus avoiding a thermal adverse influencing of the sample.

In such a vertical temperature stratification within the cooling space the warm layer preferably has a temperature that corresponds substantially to a given starting temperature of a freezing process or of a given target temperature of a thawing process whereas the cold layer has a temperature that corresponds substantially to a given target temperature of the freezing process or to a given starting temperature of the thawing process. This is advantageous because the two temperature layers in the cooling space then always have the correct temperature in order to avoid a thermal adverse influencing of the sample during the extraction of the sample and during its insertion into the sample container.

In a preferred exemplary embodiment of the invention the sample container is thermally insulated and comprises a cover that can be opened in order to move the sample and to insert the sample. The thermal insulation of the sample container is important if the tempering of the sample container takes place actively by a cooling and/or heating since the temperature adjustment in the sample container is then only minimally influenced by the ambient temperature inside the cooling space.

However, it is alternatively also possible that the sample container is not thermally insulated from the cooling space. This is especially meaningful if the tempering of the sample container does not take place actively by a heating or cooling apparatus but rather by a vertical motion of the sample container within the vertical temperature stratification of the cooling space, as already described above.

In a preferred exemplary embodiment of the invention at least one substantially vertically running shaft with a wall of a heat-conducting material is arranged in the cooling space wherein the sample container can move vertically in the shaft. The good thermal conductivity of the shaft wall advantageously results in an approximately constant vertical temperature gradient in the shaft so that a certain temperature can be associated with each height in the shaft. This advantageously makes it possible to do without temperature sensors on the sample container.

It should furthermore be mentioned that an extractable, thermally insulated transport container is arranged in the cooling space in order to extract the sample from the cooling space after the freezing or to insert it into the cooling space for thawing. At the beginning of a thawing process the sample is then extracted from the transport container and transferred into the sample container, where the sample is then thawed. In the same manner the sample is extracted from the sample container at the end of a freezing process and transferred into the transport container, that can then be extracted from the cooling space and, e.g., inserted in a cryotank.

The cooling space itself is preferably designed as a vat in the cryoapparatus in accordance with the invention and covered at its top by an extractable protective hood that is preferably at least partially transparent in order to make a visual monitoring possible.

However, there is also the alternative possibility of doing without a protective hood so that the cooling space is open at the top.

It should furthermore be mentioned that several storage surfaces can be arranged in the cooling space at different heights that correspond to different temperatures in accordance with the vertical temperature stratification in the cooling space.

Finally, it should also be mentioned that the invention comprises not only the previously described cryoapparatus in accordance with the invention but also a corresponding operating method that results from the present description.

BRIEF DESCRIPTION OF SEVERAL VIEWS OF THE DRAWINGS

Other advantageous further developments of the invention are characterized in the subclaims or are explained in detail below together with a description of the preferred exemplary embodiments of the invention using the figures.

DETAILED DESCRIPTION OF PREFERRED EMBODIMENTS

Figure 1:
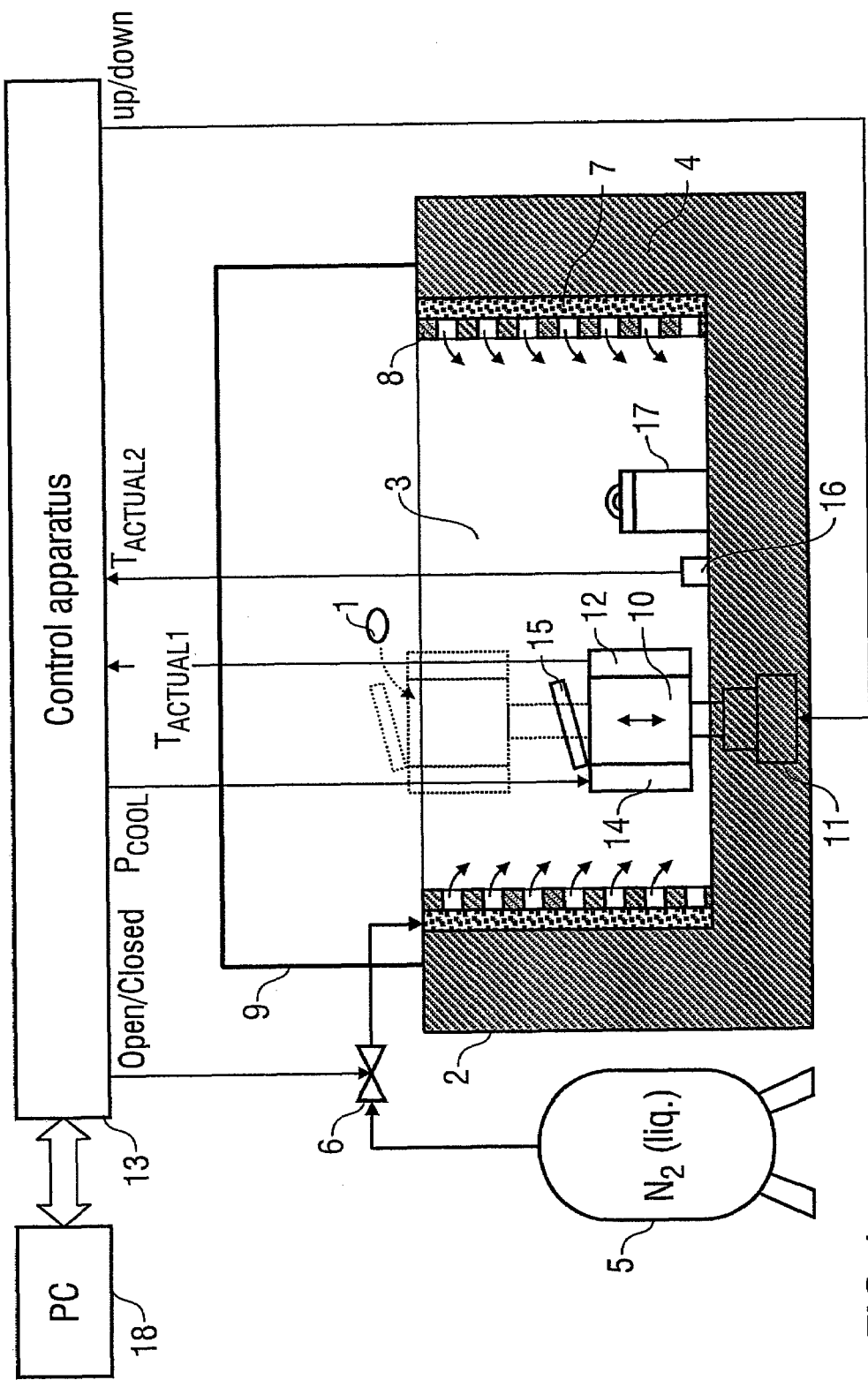
FIG. 1 shows a schematized cross-sectional view of a cryoapparatus in accordance with the invention for freezing and thawing a biological sample in a manner that maintains its vitality.

The cryoapparatus shown in FIG. 1 makes it possible to freeze and thaw a biological sample 1 while maintaining vitality in that sample 1 is cooled down or heated during freezing and thawing in accordance with given chronological temperature characteristics.

To this end, the cryoapparatus comprises a cryovat 2 that encloses a cooling space 3, the cryovat 2 comprising a wall 4 of a thermally insulating material.

The cooling of the cooling space 3 takes place by liquid nitrogen contained in a cooling agent container 5, that is represented only schematically here, and inserted via a controllable cooling agent valve 6 into the cooling space 3.

The insertion of the liquid nitrogen into the cooling space 3 takes place here indirectly via a porous buffer material 7 with which the inside of the wall 4 of the cryovat 2 is jacketed, a grating 8 of a material that conducts heat well (e.g., copper) being arranged on the inside of the buffer material 7. The buffer material 7 prevents the supplied liquid nitrogen from collecting on the bottom of the cooling space 3 in the form of a so-called nitrogen lake. Instead, the supplied liquid nitrogen is released by the buffer material 7 uniformly through the grating 8 into the cooling space 3.

The cryovat 2 is covered on its top by a removable protective bell 9, the protective bell 9 being transparent in order to make possible a visual monitoring of the cooling space 3.

A sample container 10 is present in the cooling space 3 that can be raised and lowered in the vertical direction by a lifting apparatus 11, that is represented here only schematically, as will be described in detail later.

The temperature sensor 12 is located on the sample container 10, measures the temperature $T_{ACTUAL1}$ in the sample container 10 and passes it on to the control apparatus 13, that also controls the cooling agent valve 6 and adjusts the temperature in the cooling space 3 with it.

Furthermore, the sample container 10 has a cooling apparatus 14 that is represented only schematically and cools the inner space of the sample container 10 with a cooling capacity $P_{COOL}$, given by the control apparatus 13, as will also be described in detail later. The cooling apparatus 14 can utilize, e.g., the liquid nitrogen contained in the cooling agent container 5 but other cooling techniques can also be used.

Moreover, it should be mentioned that the sample container 10 is thermally insulated and has a sealable cover 15 that is also thermally insulated, the cover 15 being opened in order to insert the sample 1 into the sample container 10 and to extract it from the sample container 10.

Furthermore, another temperature sensor 16 is arranged on the bottom of the cooling space 3 that measures the temperature $T_{ACTUAL2}$ at the bottom of the cooling space 3 and passes it on to the control apparatus 13. The control apparatus then regulates the temperature $T_{ACTUAL2}$ to a given theoretical value by appropriately controlling the cooling agent valve 6.

In addition, a removable transport container 17, that is thermally insulated and has a removable cover, is located on the bottom of the cooling space 3. The transport container 17 makes it possible to transfer the cryofrozen sample 1 from the cooling space 3 into a cryotank that is not represented here without the sample 1 being warmed up during this transfer and being thermally damaged as a result. Moreover, the transport container 17 makes it possible to transfer the cryofrozen sample 1 out of a cryotank, that is not represented here, into the cooling space 3 in order that the frozen sample 1 can be subsequently thawed in the sample container 10, which will be described in detail later.

Finally, the control apparatus 13 is connected to a traditional personal computer 18, wherein any chronological temperature characteristics for the freezing or thawing process can be programmed on the personal computer 18.

Figure 7A:
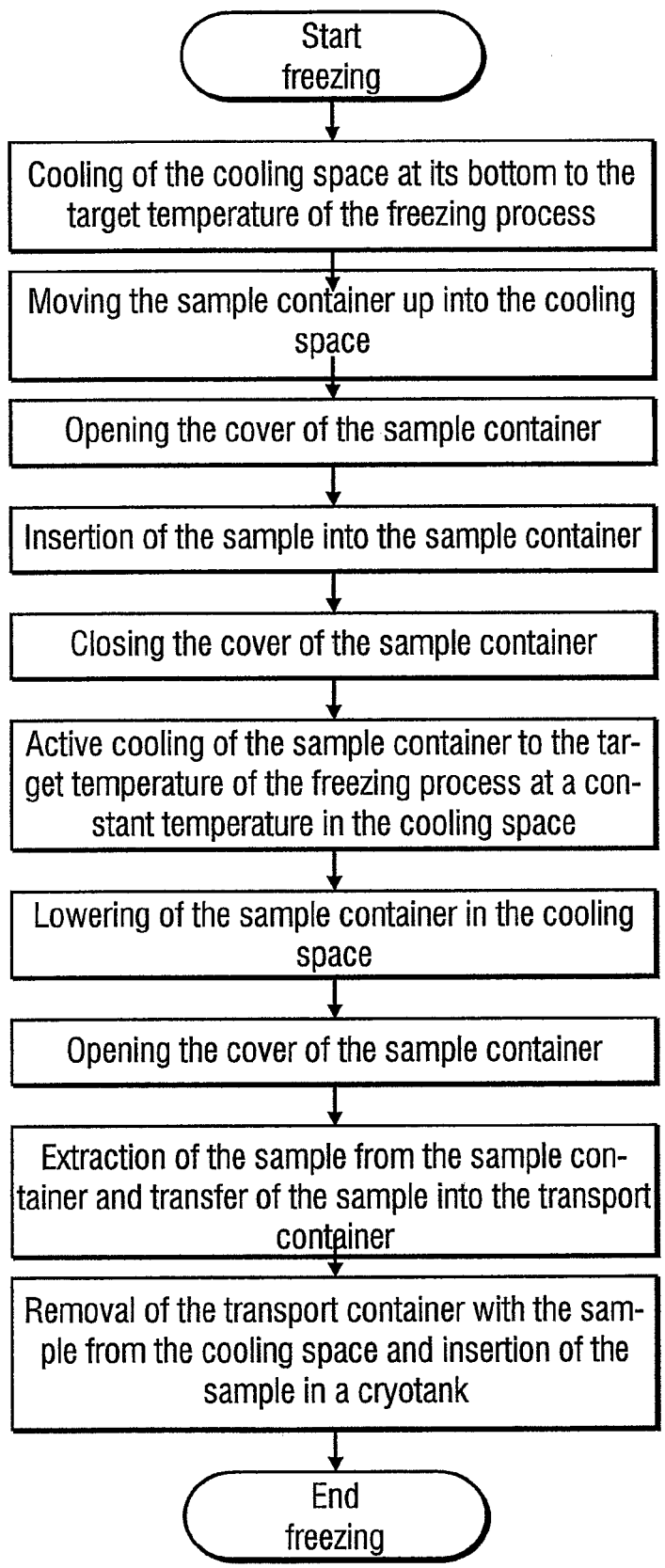
FIG. 7A shows a freezing process in the exemplary embodiment in accordance with FIG. 1 in the form of a flowchart.

A freezing process for the cryoapparatus according to FIG. 1 is described in the following with reference made to the flowchart in FIG. 7A.

In this process, the control apparatus 13 regulates temperature $T_{ACTUAL2}$ at the bottom of the cooling space 3 by suitably controlling the cooling agent valve 6 down to the given target temperature of the freezing process.

Furthermore, the empty sample container 10 is moved by the lifting apparatus 11 in the cooling space 3 upward into the position shown in dotted lines so that the mouth of the sample container 10 rests at an opening of the cover 5 above the cryovat 2.

The cover 15 of the sample container 10 is then opened, whereupon the sample 1 is inserted into the sample container 10 and the cover 15 of the sample container is closed. During this insertion of the sample 1 into the sample container 10, the sample 1 is hardly adversely affected thermally since the temperatures in this area are close to the starting temperature of the freezing process.

After the sealing of the sample container 10 its inner space is then cooled by the cooling apparatus 14, the control apparatus 13 regulating predetermined chronological temperature characteristics in that the cooling apparatus 14 regulates the cooling apparatus 14 in accordance with the temperature $T_{ACTUAL}$ measured by the temperature sensor 12.

After the conclusion of the freezing the sample container 10 is then moved down into the cooling space 3 by the lifting apparatus 11, a temperature prevailing in the lower area of the cooling space 3 that substantially corresponds to the target temperature of the freezing process. During the subsequent opening of the cover 15 and the extraction of the sample 1 from the sample container 10, the frozen sample 1 is then hardly adversely affected thermally since the surrounding medium in the cooling space 3 has almost the same temperature.

The sample 1 is then transferred after the extraction from the sample container 10 into the transport container 17, whereupon the transport container 17 with the cryofrozen sample 1 located in it is removed from the cooling space 3 and can be inserted, e.g., in a cryotank.

Figure 7B:
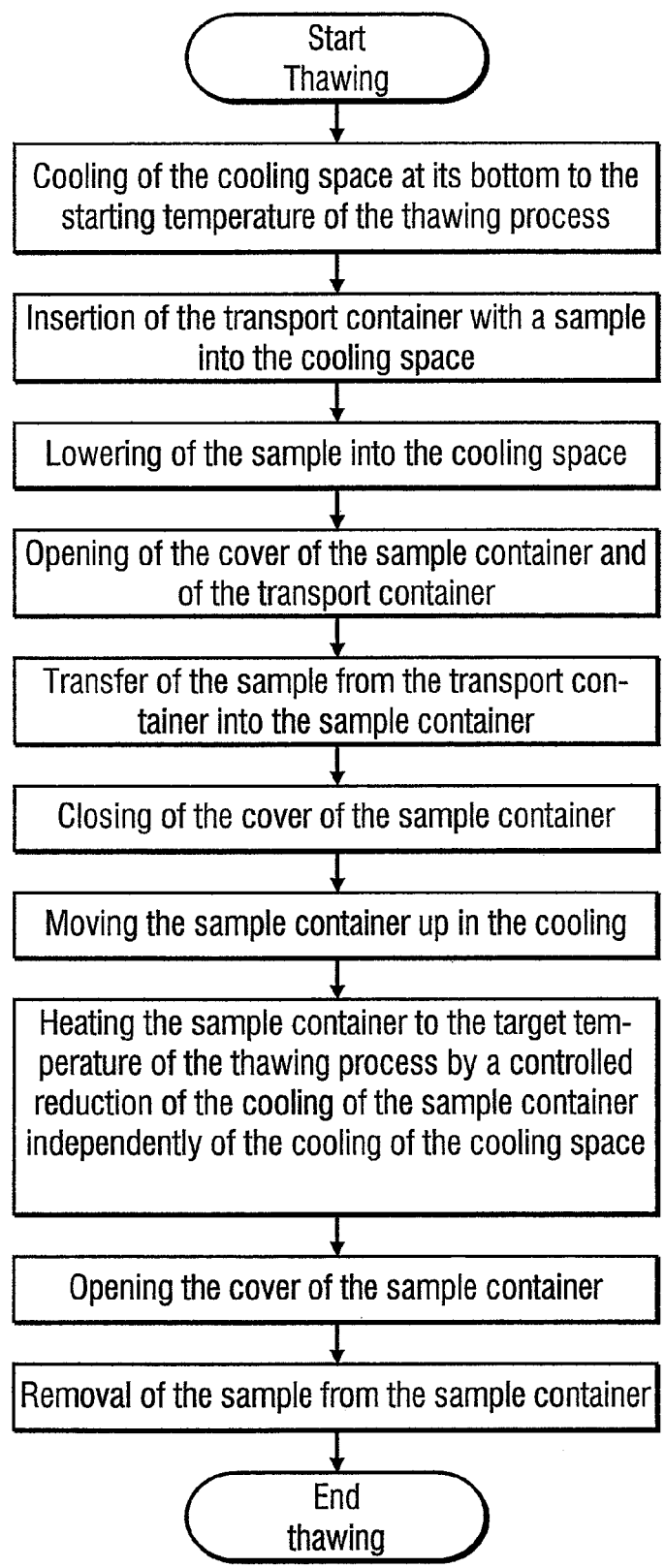
FIG. 7B shows a thawing process in the exemplary embodiment in accordance with FIG. 1 in the form of a flowchart.

A thawing process of the cryoapparatus according to FIG. 1 will be described in the following with reference made to the flowchart in FIG. 7B.

In this process, the cooling space 3 is cooled to the extent that the temperature $T_{ACTUAL2}$ at the bottom of the cooling space 3 substantially corresponds to the starting temperature of the thawing process.

The transport container 17 with the cryofrozen sample 1 located in it is then subsequently extracted from a cryotank that is not represented here and placed on the bottom of the cooling space 3.

Then, the cover 15 of the sample container 10 is opened just as the cover of the transport container 17 is also opened.

The sample 1 located in the transport container 17 is then extracted from the transport container 17 and transferred into the sample container 10, whereupon the cover 15 of the sample container 10 is then closed. During the transfer of the sample 1 from the transport container 17 into the sample container 10, the sample 1 is hardly adversely affected thermally since the temperatures at the bottom of the cooling space 3 are substantially equal to the temperature of the sample 1.

After the sealing of the sample container 10, the sample container 10 is then moved vertically upward into the position shown in dotted lines by the lifting apparatus 11 in the cooling space 3.

The inner space of the sample container 10 is subsequently heated to predetermined chronological temperature characteristics by reducing the cooling capacity $P_{COOL}$ of the cooling apparatus 14, the control apparatus 13 regulating the cooling capacity $P_{COOL}$ as a function of the measured temperature $T_{ACTUAL1}$ in order to attain the desired chronological temperature characteristics in the sample container 10 during the thawing of the sample 1.

After the end of the thawing process the cover 15 of the sample container 10 is then opened, whereupon the thawed sample 1 is extracted from the sample container 10.

The sample 1 is hardly adversely affected thermally by the surrounding medium even in this extraction of the thawed sample 1 from the sample container 10 since the temperatures in this area are relatively high.

Figure 2:
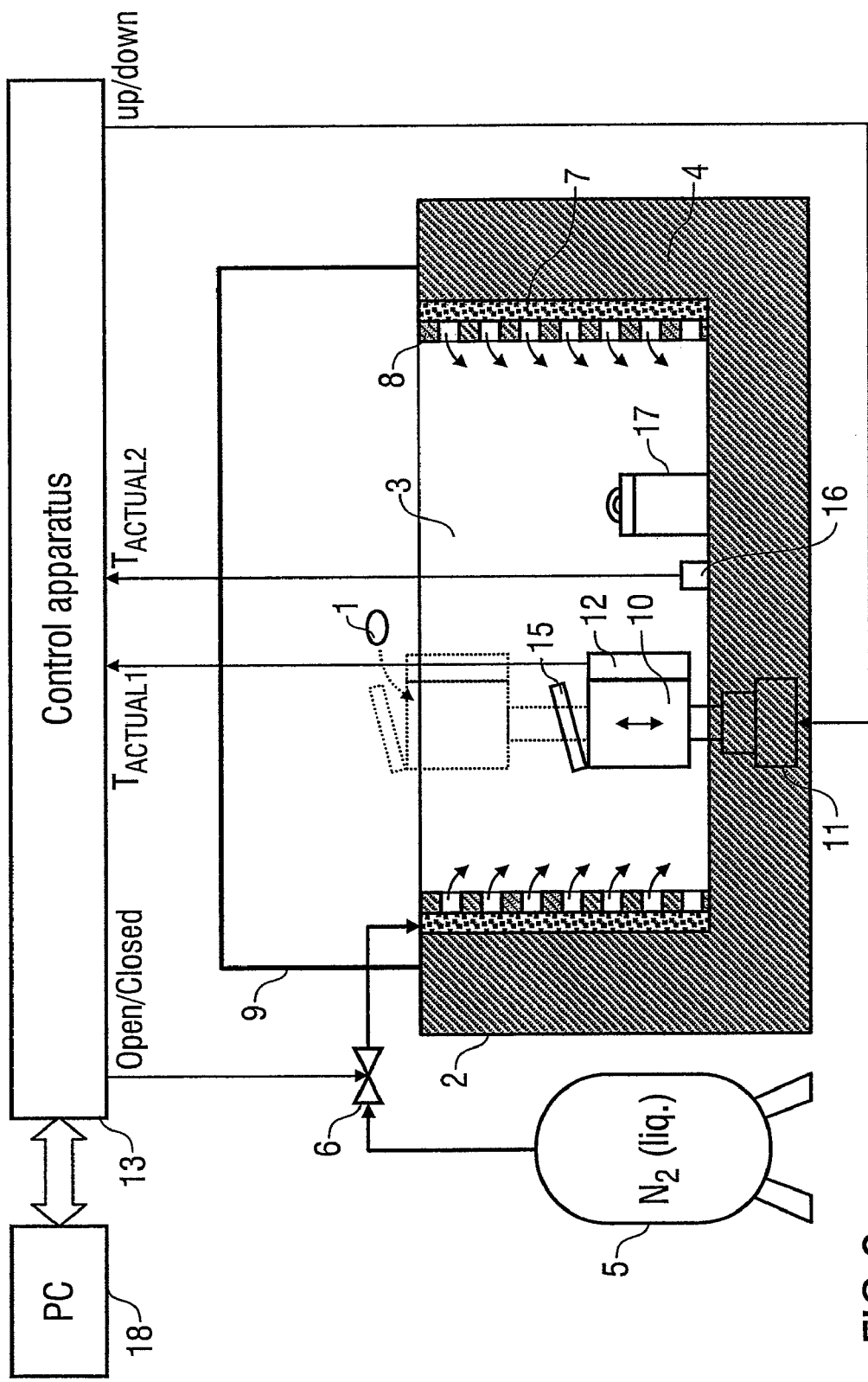
FIG. 2 shows a schematized cross-sectional view of a modified exemplary embodiment of a cryoapparatus in accordance with FIG. 1.

The alternative exemplary embodiment of a similar cryoapparatus shown in FIG. 2 will now be described in the following, which largely coincides with the previously described exemplary embodiment of a cryoapparatus shown in FIG. 1. In order to avoid repetitions the previous description is therefore extensively referred to, wherein the same reference numerals are used for corresponding components.

This exemplary embodiment has the particularity that the cryoapparatus does not have a separate, actively operating cooling apparatus 14.

Instead, the tempering of the sample container 10 takes place here by a vertical lowering or raising of the sample container 10 in the cooling space 3. Due to the vertical temperature stratification in the cooling space 3 the temperature in the sample container 10 also changes so that given chronological temperature characteristics can also be adjusted during the thawing or freezing of the sample. The lowering or raising of the sample container 10 takes place here controlled by the control apparatus 13 as a function of the temperature $T_{ACTUAL1}$ in the sample container 10 measured by the temperature sensor 12.

In contrast to the exemplary embodiment in accordance with FIG. 1, the sample container 10 is not thermally insulated here in order that the inner space of the sample container 10 can assume, as a function of its particular height inside the cooling space 3, the associated temperature.

Figure 8A:
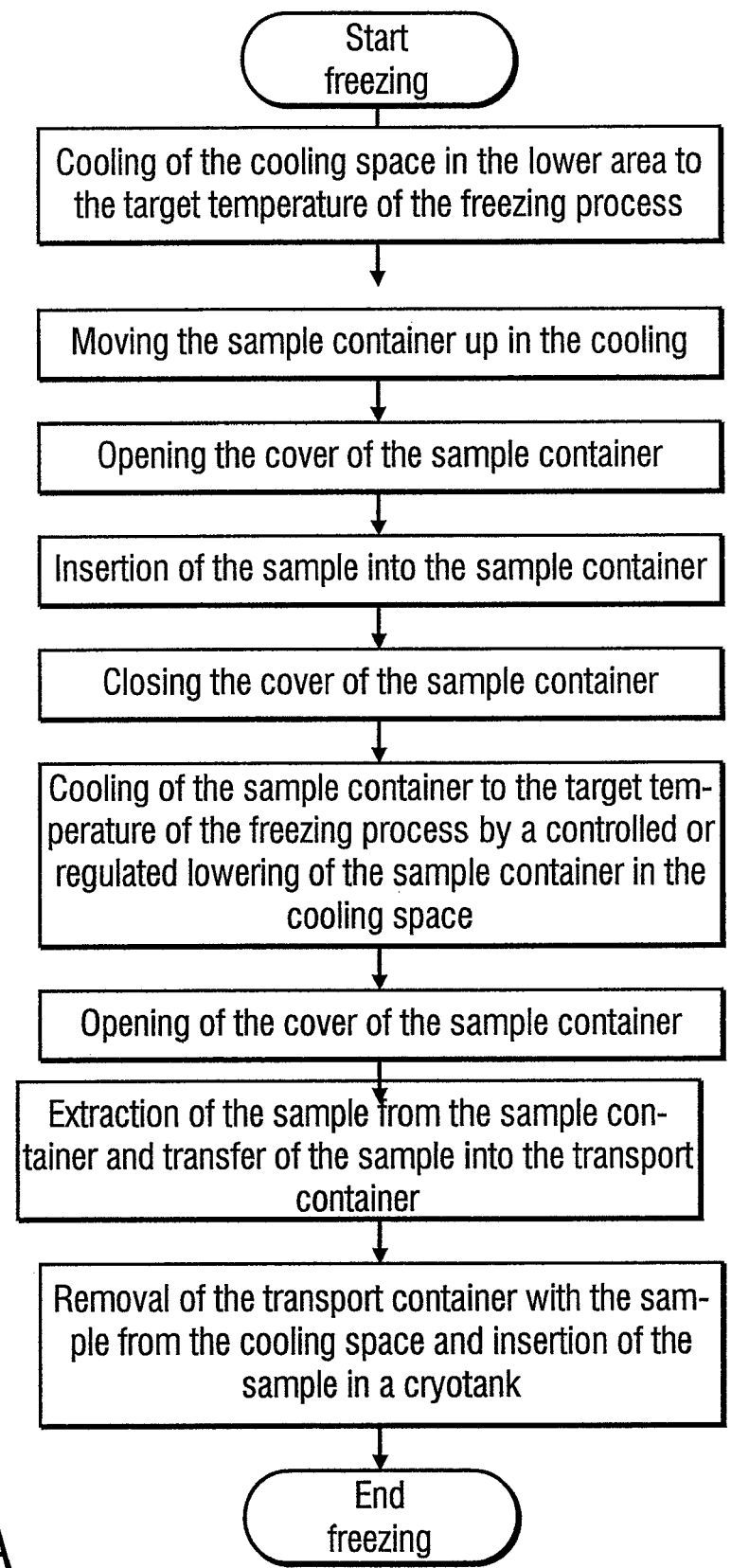
FIG. 8A shows a freezing process in the exemplary embodiment in accordance with FIGS. 2 and 5A, 5B in the form of a flowchart.
Figure 8B:
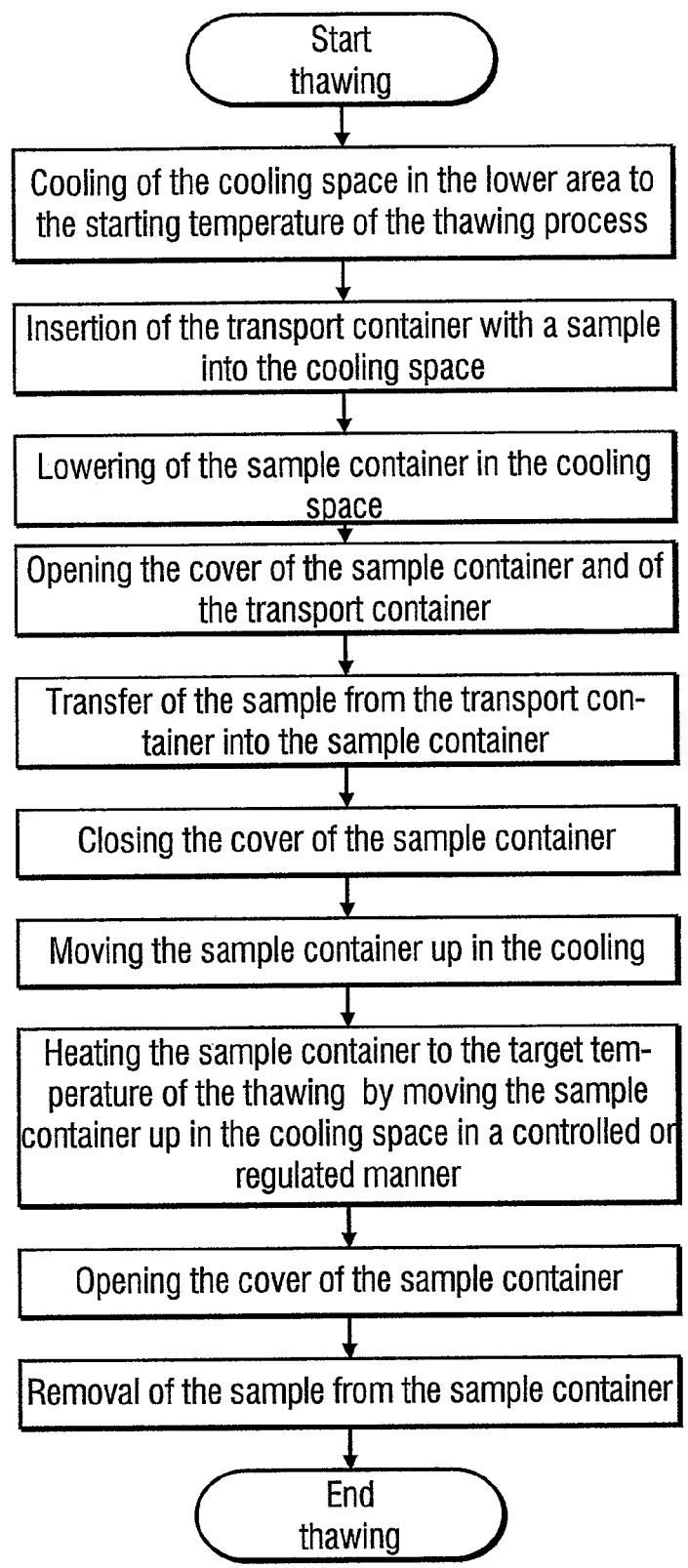
FIG. 8B shows a thawing process in the exemplary embodiments in accordance with FIGS. 2 and 5A, 5B.

The characteristics of the freezing process results here from the flowchart according to FIG. 8A whereas the characteristics of a thawing process is shown in the flowchart according to FIG. 8B.

The alternative exemplary embodiment of a cryoapparatus in accordance with the invention and shown in FIG. 3 will now be described in the following, which cryoapparatus coincides partially with the previously described exemplary embodiment so that in order to avoid repetitions the previous description is therefore referred to, wherein the same reference numerals are used for corresponding components.

A particularity of this exemplary embodiment is at first that the sample container 10 is stationarily arranged in the cooling space 3 on the bottom of the cooling space 3 so that the lifting apparatus 11 can be dispensed with.

Another particularity of this exemplary embodiment is that a heating apparatus 19 is attached to the inner wall of cooling space 3 in its upper area and heats the upper partial area of cooling space 3.

The heating apparatus 19 is turned on by the control apparatus 13 before a sample is inserted into the sample container 10 at the beginning of a freezing process. This heats the upper partial area of the cooling space 3, which prevents thermal damage to the sample during the insertion into the sample container 10.

Moreover, the heating apparatus 19 is also turned on by the control apparatus 13 before a thawed sample is extracted at the end of a thawing process from the sample container. This also prevents the thawed sample from being thermally damaged during the extraction from the sample container 10.

In contrast thereto, the heating apparatus 19 is turned off when the sample is extracted from the sample container 10 at the end of a freezing process and transferred into the transport container 17.

In addition, the heating apparatus 19 is also turned off when the sample is transferred at the beginning of a thawing process from the transport container 17 into the sample container 10.

This turning off of the heating apparatus 19 prevents for its part an adverse thermal influencing of the cryocooled sample during the transfer between the sample container 10 and the transport container 17.

Figure 3:
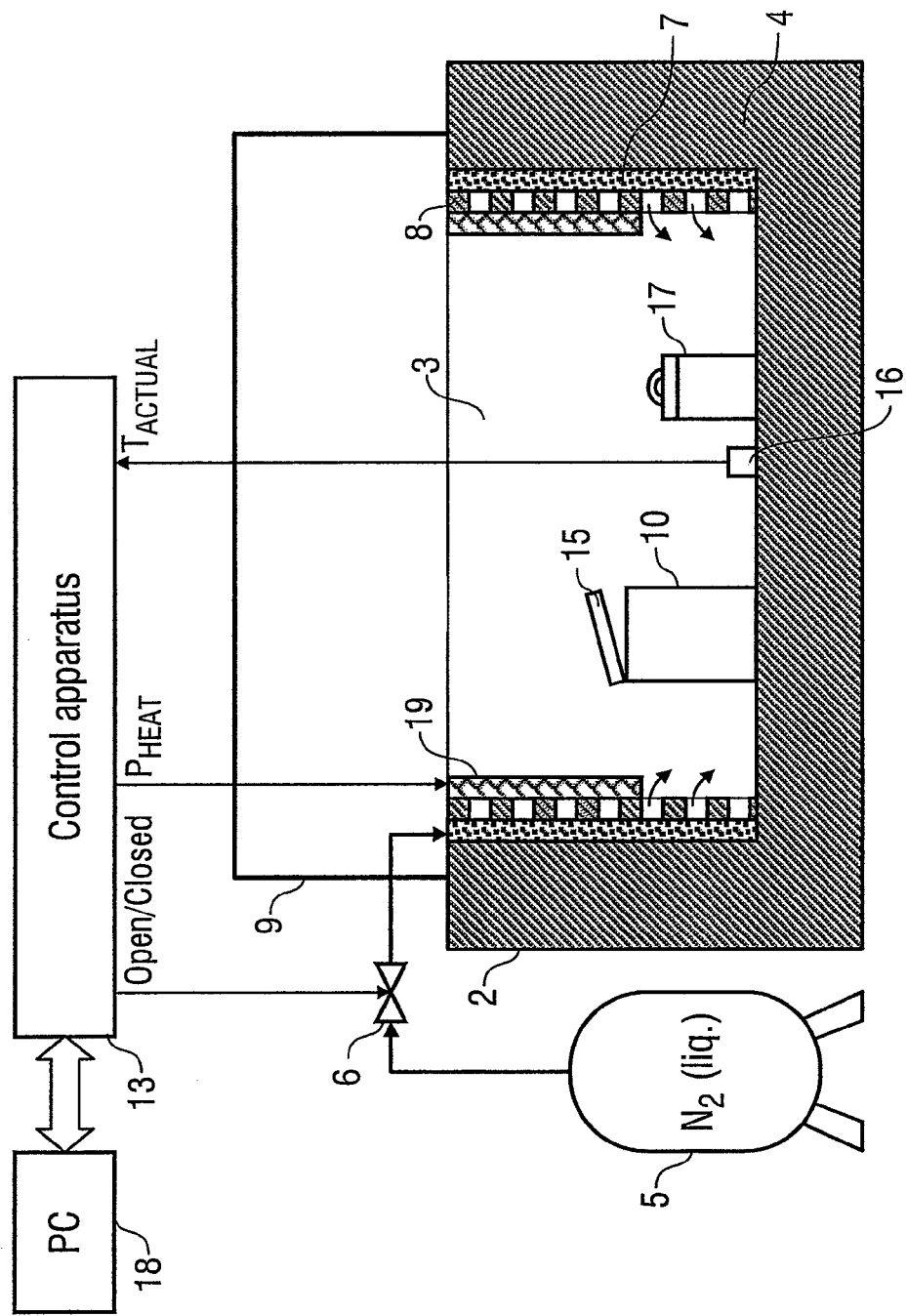
FIG. 3 shows a schematized cross-sectional view of an alternative exemplary embodiment of a cryoapparatus in accordance with the invention with an additional heating apparatus.
Figure 4:
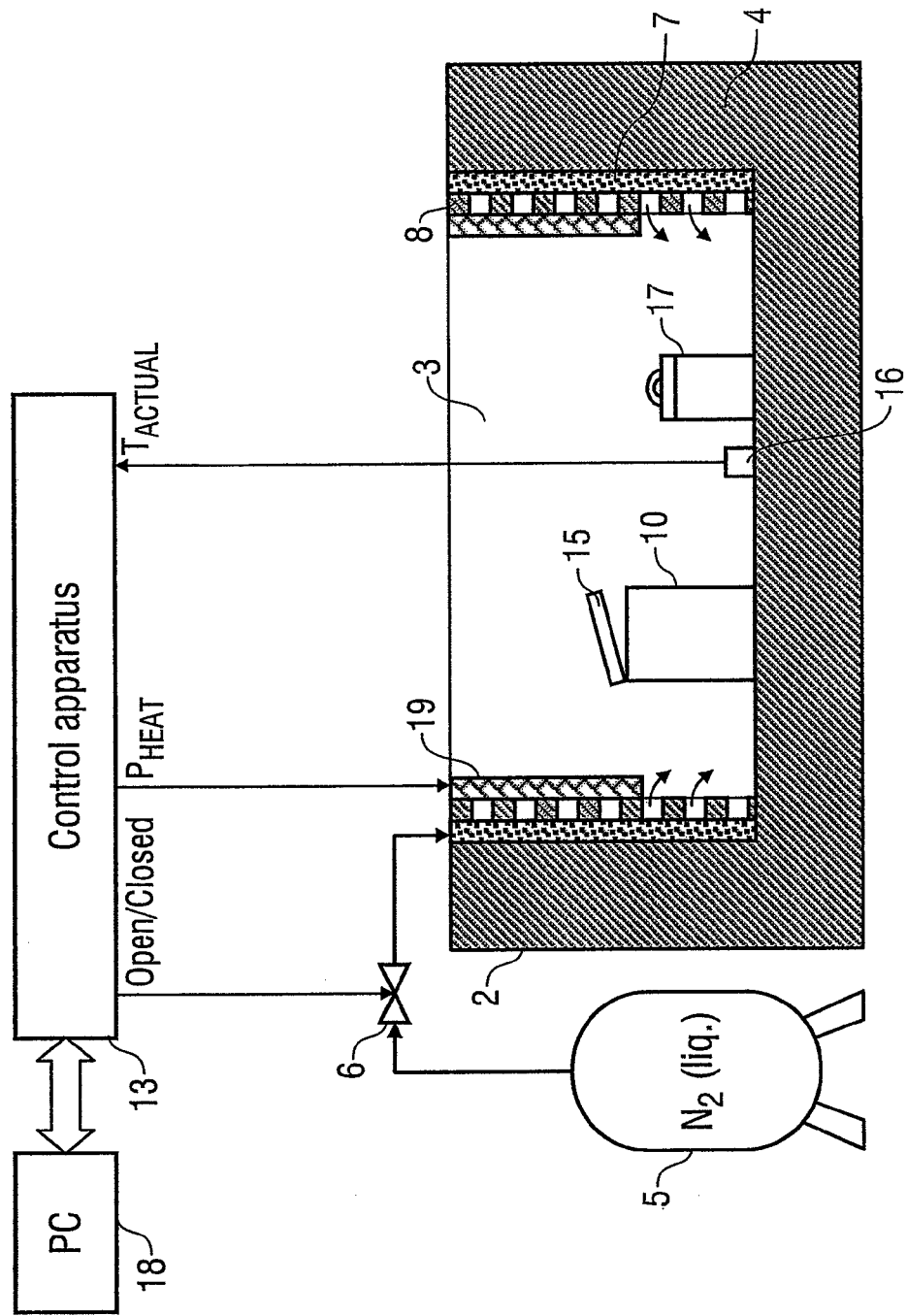
FIG. 4 shows a schematized cross-sectional view of a simplified exemplary embodiment of such a cryoapparatus that in contrast to the other cryoapparatuses does not have a protective hood.

The alternative exemplary embodiment shown in FIG. 4 coincides almost completely with the previously described exemplary embodiment shown in FIG. 3. Only the protective bell 9 was omitted.

Figure 5A:
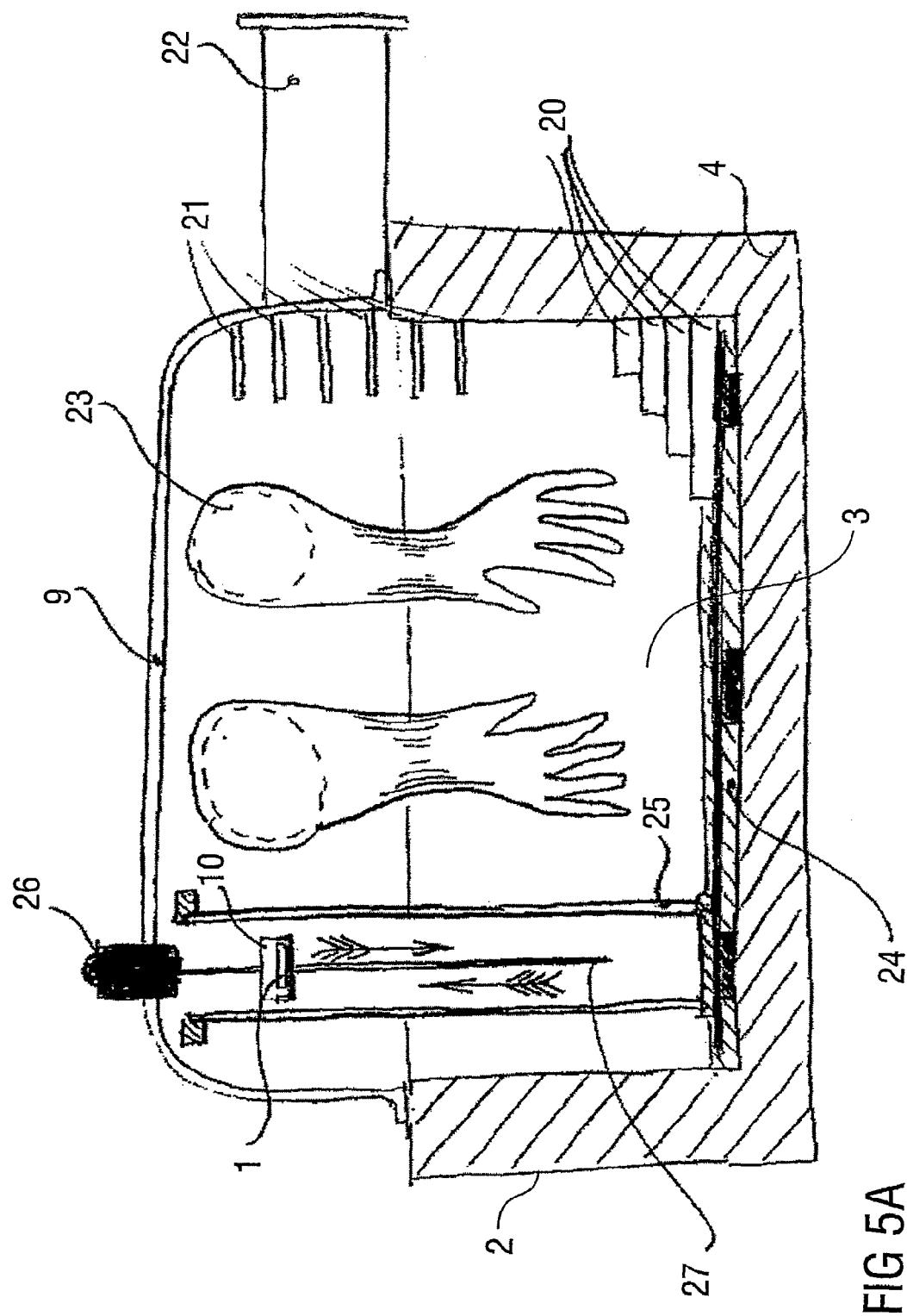
FIG. 5A shows a simplified cross-sectional view of another exemplary embodiment of a cryoapparatus in accordance with the invention.

The alternative exemplary embodiment of a cryoapparatus in accordance with the invention shown in FIGS. 5A and 5B and coinciding in part with the previously described exemplary embodiments will now be described in the following, so that in order to avoid repetitions the previous description is partially referred to, wherein corresponding components are characterized by the same reference numerals.

A particularity of this exemplary embodiment is that several stepped storage surfaces 20 are arranged on the bottom of the cooling space 3 on which cryosubstrates can be temporarily stored. Due to the vertical temperature stratification in the cooling space 3, the individual storage surfaces 20 are located at different temperatures so that a stepped temperature profile can be successively moved through in time in that a cryosample is stored successively on the different storage surfaces 20.

Another particularity of this exemplary embodiment is that several shelf-like storage surfaces 21 are arranged superposed in the upper area of the cooling space 3 that also have different temperatures due to the vertical temperature stratification in the cooling space 3 and make it possible to store a sample.

Furthermore, the cryoapparatus in this exemplary embodiment has a lock 22 via which the samples can be brought into the cooling space 3 and extracted from the cooling space 3.

Moreover, the protective bell 9 is provided with intervention zones 23 with which an operator can perform manipulations in the cooling space 3.

The cooling of the cooling space 3 takes place here by a nitrogen lake 24 produced on the bottom of the cooling space 3.

The tempering of the sample 1 in the form of a cryosubstrate in the sample container 10 takes place here, however, in a different manner, as will be described in the following.

To this end, a vertically running shaft 25 is arranged in the cooling space 3 which shaft consists of a good heat-conductive material (e.g., copper) and an approximately constant vertical temperature gradient is produced in the shaft 25 due to the good heat conductivity.

The sample container 10 can be raised or lowered in a vertical direction by a motor 26 via a rotatable spindle 27 in the shaft 25 in order to temper the sample container 10 in accordance with the vertical temperature stratification in the sample space 3.

It is furthermore apparent from FIG. 5B that several temperature sensors 28-31 are arranged above and below the sample container 10 at different heights and measure a local vertical temperature gradient, wherein the temperature sensors 28-31 are connected to a regulating apparatus that controls the motor 26 in such a manner that the sample container 10 is always located at the right height in the cooling space 3 in order that the desired chronological temperature characteristics are achieved during the freezing and thawing of sample 1.

Figure 5B:
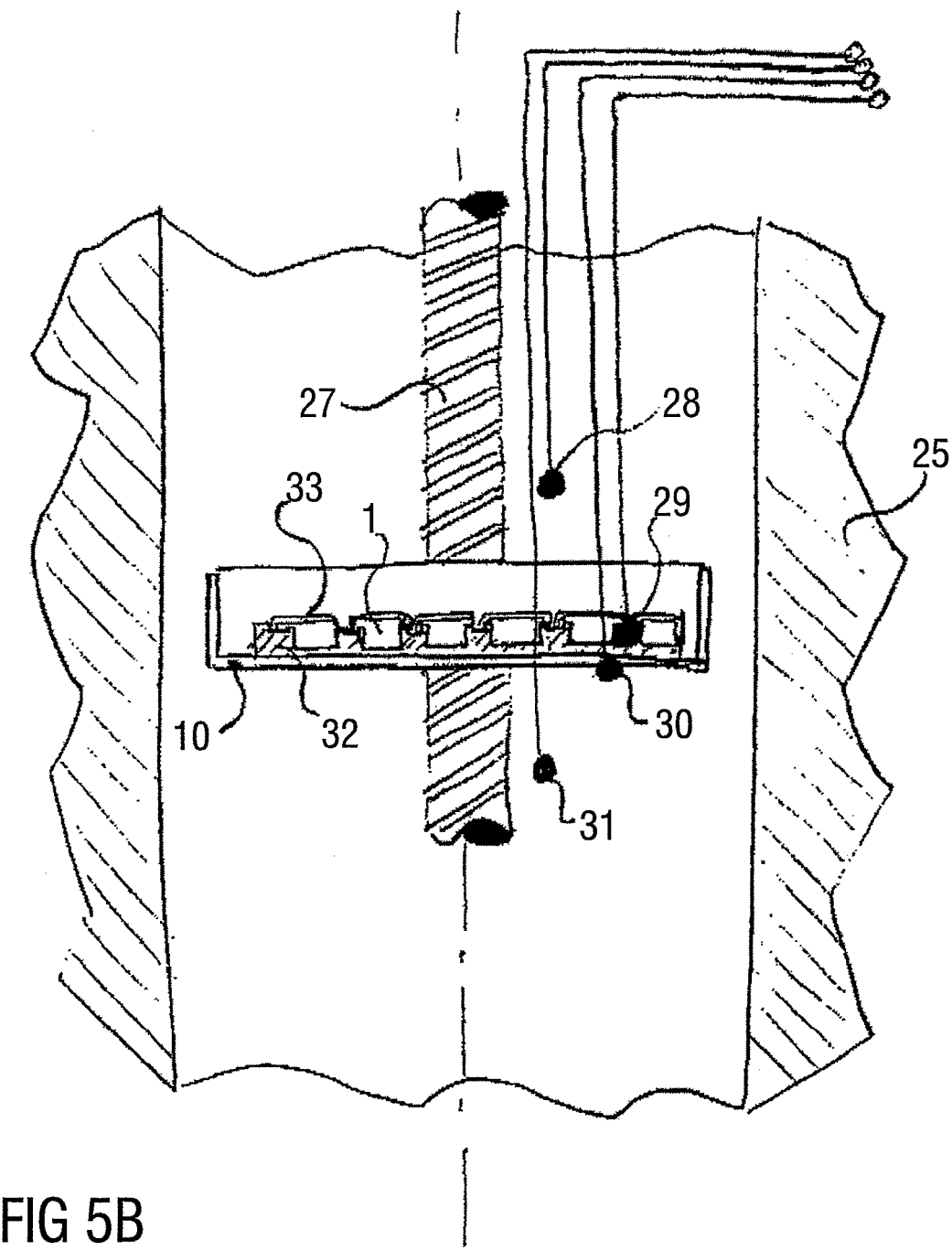
FIG. 5B shows a cross-sectional view of a lifting apparatus of the cryoapparatus in FIG. 5A for lifting or lowering the sample.

Furthermore, the enlarged cross-sectional view in FIG. 5B shows that the carriage-shaped sample container 10 contains a cryosubstrate 32 and a cover 33 and containers for the samples 1.

Figure 6:
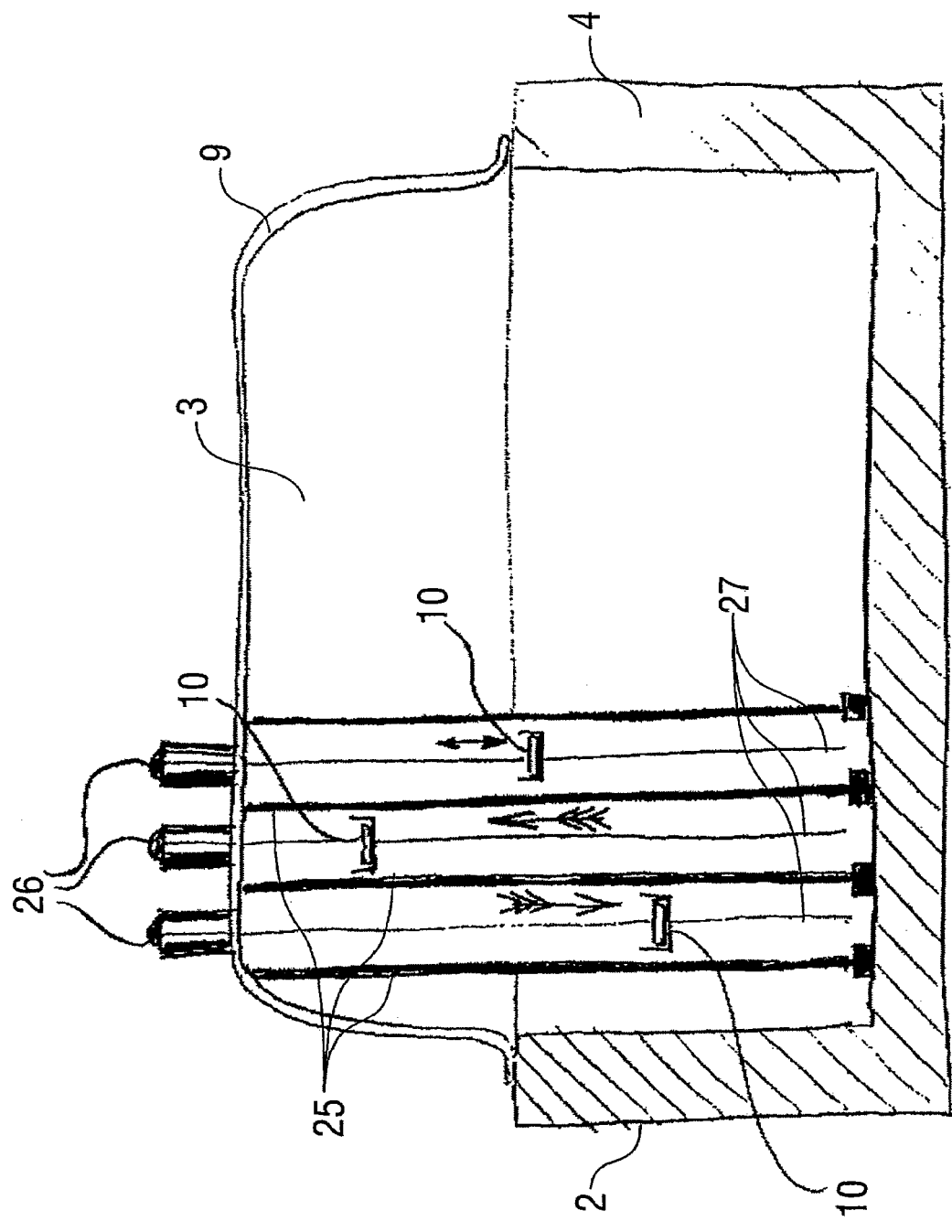
FIG. 6 shows a simplified cross-sectional view of another exemplary embodiment of a cryoapparatus in accordance with the invention with several lifting apparatuses for the simultaneous freezing or thawing of several samples independently of each other.

The alternative exemplary embodiment shown in FIG. 6 will now be described that largely coincides with the previously described exemplary embodiment shown in FIGS. 5A and 5B, so that in order to avoid repetitions the previous description of these figures is extensively referred to, wherein the same reference numerals are used for corresponding components.

A particularity of this exemplary embodiment is that several shafts 25 are arranged adjacent to each other in the cooling space 3 in each of which a sample container 10 can be raised and lowered in a vertical direction in order to adjust the desired temperature in accordance with the vertical temperature stratification in the cooling space 3. This arrangement advantageously makes possible parallel freezing and thawing processes on several samples.

The invention is not limited to the previously described preferred exemplary embodiments but rather a plurality of variants and modifications is possible that also makes use of the inventive concept and therefore falls within its scope of protection.

The invention claimed is:

1. A cryoapparatus for freezing and thawing a sample, comprising:
    (a) a coolable cooling space,
    (b) a sample container arranged in the cooling space for temporarily receiving the sample when freezing or thawing the sample,
    (c) a thermally insulated, extractable transport container that is arranged in the cooling space for extracting the sample from the cooling space after the freezing and for inserting the sample into the cooling space for thawing,
    (d) sample transferring means for transferring within the cooling space the sample out of the sample container and into the transport container and out of the transport container and into the sample container,
    (e) temperature adjusting means for adjusting a temperature of the sample container separately from the cooling space between the insertion of the sample and the extraction of the sample, and
    (f) cooling means for cooling a lower area of the cooling space to a given target temperature of a freezing process so as to cool the sample container from a given starting temperature of the freezing process to the target temperature of the freezing process.

2. The cryoapparatus according to claim 1, further comprising a lifting apparatus with which the sample container can be lowered and raised in the cooling space in a controlled or regulated manner.

3. The cryoapparatus according to claim 1, wherein the sample container has a temperature sensor that measures a temperature in the sample container.

4. The cryoapparatus according to claim 3, wherein several temperature sensors are attached to the sample container at different vertical distances in order to determine a local vertical temperature gradient in the cooling space.

5. The cryoapparatus according to claim 1, wherein the sample container is stationarily arranged on a bottom of the cooling space.

6. The cryoapparatus according to claim 1, further comprising a heating apparatus for heating the cooling space.

7. The cryoapparatus according to claim 6, wherein the heating apparatus heats only an upper partial area of the cooling space.

8. The cryoapparatus according to claim 1, further comprising a vertical temperature stratification in the cooling space with a lower cold layer and an upper warm layer.

9. The cryoapparatus according to claim 8, wherein the warm layer has a temperature that corresponds substantially to a given starting temperature of a freezing process whereas the cold layer has a temperature that corresponds substantially to a given target temperature of the freezing process.

10. The cryoapparatus according to claim 1, wherein the cooling space is cooled by a first cooling apparatus and the sample container is cooled by a second cooling apparatus.

11. The cryoapparatus according to claim 10, further comprising a control apparatus, wherein the control apparatus is connected on an output side to the first cooling apparatus and to the second cooling apparatus and adjusts a cooling capacity of the cryoapparatus, whereas the control apparatus is connected on an input side to a temperature sensor of the sample container.

12. The cryoapparatus according to claim 1, wherein the sample container is thermally insulated and has a cover that can be opened in order to extract the sample and in order to insert the sample and can be closed in order to thermally insulate the sample container during cooling.

13. The cryoapparatus according to claim 1, wherein the sample container is not thermally insulated against the cooling space.

14. The cryoapparatus according to claim 1, wherein a substantially vertically running shaft with a wall of a heat-conducting material is arranged in the cooling space, wherein the sample container can move vertically in the shaft.

15. The cryoapparatus according to claim 1, wherein the transport container is arranged on a bottom of the cooling space.

16. The cryoapparatus according to claim 1, wherein the cooling space is vat-shaped and is covered on top by a removable protective hood.

17. The cryoapparatus according to claim 16, wherein the protective hood is at least partially transparent.

18. The cryoapparatus according to claim 1, wherein several storage surfaces are arranged in the cooling space at different heights that correspond to different temperatures.

19. An operating method for a cryoapparatus, comprising the following steps:
    (a) insertion of the sample into a sample container arranged in a coolable cooling space,
    (b) adjusting a temperature of the sample present in the sample container,
    (c) extraction of the sample from the sample container, wherein the sample container is temperature adjusted separately from the cooling space between the insertion of the sample and the extraction of the sample, and in order to freeze the sample:
        a lower area of the cooling space is cooled down to a given target temperature of a freezing process,
        the sample container is cooled down from a given starting temperature of the freezing process to the target temperature of the freezing process, the sample is transferred, after attaining the target temperature, into a thermally insulated transport container located in the cooling space and the transport container containing the sample is extracted from the cooling space, and in order to thaw the sample:

the lower area of the cooling space is cooled down to a given target temperature of a freezing process, a thermally insulated transport container containing the sample is inserted into the cooling space, the sample is transferred out of the transport container into the sample container, the sample container is heated from a given starting temperature of a thawing process to a given target temperature of the thawing process, and the sample is extracted from the sample container after the target temperature of the thawing process has been attained.

20. The operating method according to claim 19, wherein the sample container is raised and lowered in the cooling space.

21. The operating method according to claim 19, wherein a temperature of the sample container is adjusted by raising or lowering the sample container in the cooling space in a controlled or regulated manner.

22. The operating method according to claim 19, wherein the sample container is actively cooled by a cooling apparatus.

23. The operating method according to claim 19, wherein a vertical temperature stratification with an upper warm layer and a lower cold layer is generated in the cooling space.

24. The operating method according to claim 23, wherein the warm layer is brought to a temperature that corresponds substantially to a given starting temperature of a freezing process, whereas the cold layer is brought to a temperature that corresponds substantially to a given target temperature of the freezing process.

25. The operating method according to claim 19, wherein the cooling space is actively heated.

26. The operating method according to claim 25, wherein the cooling space is actively heated only in an upper partial area.

27. The cryoapparatus according to claim 8, wherein the warm layer has a temperature that corresponds substantially to a given target temperature of a thawing process whereas the cold layer has a temperature that corresponds substantially to a given starting temperature of the thawing process.

28. The operating method according to claim 23, wherein the warm layer is brought to a temperature that corresponds substantially to a given target temperature of a thawing process, whereas the cold layer is brought to a temperature that corresponds substantially to a given starting temperature of the thawing process.

* * * * *